(12) United States Patent
Gundu et al.

(10) Patent No.: US 8,852,635 B2
(45) Date of Patent: Oct. 7, 2014

(54) PHARMACEUTICAL COMPOSITIONS OF FENOFIBRATE

(75) Inventors: Ramakant Kashinath Gundu, Ahmednagar (IN); Narayanan Murali, Chennai (IN); Girish Kumar Jain, Delhi (IN)

(73) Assignee: Wockhardt Ltd, Bandra-Kurla Complex, Bandra East, Mumbai (IN)

( * ) Notice: Subject to any disclaimer, the term of this patent is extended or adjusted under 35 U.S.C. 154(b) by 946 days.

(21) Appl. No.: 12/528,628

(22) PCT Filed: Feb. 23, 2008

(86) PCT No.: PCT/IB2008/000405
§ 371 (c)(1),
(2), (4) Date: Jun. 24, 2010

(87) PCT Pub. No.: WO2008/104846
PCT Pub. Date: Sep. 4, 2008

(65) Prior Publication Data
US 2010/0255095 A1  Oct. 7, 2010

(30) Foreign Application Priority Data
Feb. 26, 2007  (IN) .......................... 372/MUM/2007

(51) Int. Cl.
*A61K 9/24* (2006.01)
*A61K 9/16* (2006.01)
*A61K 9/20* (2006.01)
*A61K 31/216* (2006.01)

(52) U.S. Cl.
CPC ............. *A61K 9/2031* (2013.01); *A61K 9/1641* (2013.01); *A61K 9/2077* (2013.01); *A61K 31/216* (2013.01)
USPC .......................................... 424/472; 514/543

(58) Field of Classification Search
CPC .................................................... A61K 9/1641
USPC .......................................... 424/472; 514/543
See application file for complete search history.

(56) References Cited

U.S. PATENT DOCUMENTS

2004/0058009 A1   3/2004  Ryde et al.

FOREIGN PATENT DOCUMENTS

| CA | 2214895 A1 | 9/1998 |
| EP | 1364646 A | 9/2003 |
| WO | WO96/21439 A | 7/1996 |
| WO | WO02/11699 A1 | 2/2002 |

*Primary Examiner* — Jake Vu
(74) *Attorney, Agent, or Firm* — Bio Intellectual Property Services LLC(Bio IPS); O. (Sam) Zaghmout

(57) ABSTRACT

The invention relates to pharmaceutical compositions comprising unmicronized fenofibrate in admixture with a wetting agent and one or more pharmaceutically acceptable excipients, wherein the admixture is not comicronized before processing. The invention also relates to processes for the preparation of such compositions.

2 Claims, No Drawings

PHARMACEUTICAL COMPOSITIONS OF FENOFIBRATE

FIELD OF THE INVENTION

The invention relates to pharmaceutical compositions comprising unmicronized fenofibrate in admixture with one or more wetting agents and one or more pharmaceutically acceptable excipients, wherein the admixture is not comicronized before processing. The invention also relates to processes for the preparation of such compositions.

BACKGROUND OF THE INVENTION

Fenofibrate is a lipid-regulating agent and belongs to the family of fibrates or fibric acid derivatives. It is indicated as an adjunctive therapy to diet for the treatment for adult patients with very high elevations of serum triglyceride levels who are at risk of pancreatitis and who do not respond adequately to dietary control. It is particularly useful for the treatment of adult endogenous hyperlipidemia, hypercholesterolemia and hypertriglyceridemia. It is commercially available as oral capsules containing micronized fenofibrate in the strengths of 67 mg, 134 mg and 200 mg Fenofibrate is practically insoluble in water and exhibits a low rate of dissolution in aqueous media that results in inadequate bioavailability after oral ingestion. This low rate of dissolution of fenofibrate in aqueous media is also found in gastrointestinal fluids. Chemically, fenofibrate is 2-[4-(4-Chlorobenzoyl)phenoxy]-2-methylpropanoic acid 1-methylethyl ester of Formula I. Several methods of increasing the rate of dissolution of drugs having low solubility in water and other aqueous media have been disclosed in the prior art.

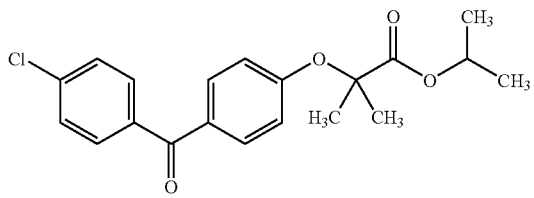

Formula I

U.S. Pat. Nos. 5,145,684; 6,375,986; 6,969,529; and 6,592,903 disclose nanoparticulate compositions of fenofibrate.

U.S. Pat. Nos. 6,277,405; 6,652,881; 7,037,529; 7,041,319; 6,589,552; 6,531,158 and U.S. Patent Application Nos. 20040057998; 20040058005 and 2004137055 disclose micronized fenofibrate compositions.

U.S. Pat. Nos. 4,895,726, 5,880,148 and U.S. Application No. 20040071771 describe co-micronizing the fenofibrate with surface-active agents.

U.S. Pat. No. 6,555,135 describes co-micronized mixture of fenofibrate with pharmaceutically acceptable excipient that is not a surfactant.

U.S. Pat. Nos. 6,074,670 and 6,277,405 disclose micronized fenofibrate coated onto hydrosoluble carriers with optional surface-active agents.

U.S. Pat. No. 6,828,334 describes inclusion complex of fenofibrate with cyclodextrins.

U.S. Pat. No. 6,027,747 describes solid dispersion of fenofibrate.

U.S. Patent Application No. 20040087656 describes fenofibrate of particle size less than 2000 nm with an improved bioavailability.

U.S. Patent Application Nos. 20060222706 and 20060222707 describe fenofibrate in intimate association with menthol or surfactant mixture.

U.S. Patent Application No. 20030138496 micronized fenofibrate with inert hydrosoluble carriers.

Several other patents and applications describe specific formulations of micronized fenofibrate with specific polymeric or surface-active agent additives while several others describe emulsion and suspension formulations of fenofibrate.

The solubility of an active pharmaceutical ingredient influences the bioavailability of the drug. Fenofibrate is a poorly soluble drug. Due to its poor hydrosolubility, fenofibrate poses problem of low dissolution. It is also poorly absorbed in the digestive tract and consequently its bioavailability is incomplete and irregular. Clearly, there is a need for improved compositions in which the fenofibrate exhibits better dissolution properties.

SUMMARY OF THE INVENTION

In one general aspect there is provided a pharmaceutical composition comprising unmicronized fenofibrate or a salt thereof in admixture with one or more wetting agents and one or more pharmaceutically acceptable excipients, wherein the admixture is not comicronized before processing.

In another general aspect of the invention there is provided a process for preparing a pharmaceutical composition of fenofibrate. The process includes:
  a) mixing unmicronized fenofibrate with one or more wetting agents and optionally with other pharmaceutically acceptable excipients;
  b) converting the pre-mix of step a) into granules; and
  c) converting the granules of step b) into a suitable dosage form.

In another general aspect of the invention there is provided a pharmaceutical composition comprising unmicronized fenofibrate or a salt thereof in admixture with one or more wetting agents and one or more pharmaceutically acceptable excipients, wherein the mixture is not comicronized before processing and wherein the formulation exhibits a dissolution profile such that more than 75% of fenofibrate is released within first 30 minutes, wherein the release rate is measured in Apparatus 2 (USP, Dissolution, paddle, 50 rpm) using 1000 ml of 0.05M SLS in water at 37° C.±0.5° C.

Embodiments of the pharmaceutical composition may include one or more of the following features. For example, the pharmaceutically acceptable excipients may include one or more of fillers, binders, lubricants, sweeteners, coloring and flavoring agents, glidants, disintegrants, and the like.

The details of one or more embodiments of the inventions are set forth in the description below. Other features, objects and advantages of the inventions will be apparent from the description and claims.

DETAILED DESCRIPTION OF THE INVENTION

Fenofibrate is practically insoluble in water. This insolubility characteristic causes fenofibrate to exhibit a low rate of dissolution in aqueous media, e.g., gastrointestinal fluids, which results in inadequate bioavailability after oral ingestion. The inventors while working on the fenofibrate formulation have surprisingly found that when fenofibrate is mixed with a wetting agent, it results in increased solubility of fenofibrate in aqueous fluids which in turn leads to significant increase in bioavailability. It was further observed that there is no need to co-micronize the mixture to increase the surface area.

Suitable wetting agents may be one or more of anionic, cationic or non-ionic surface-active agents or surfactants. Wetting agent may further include one or more of gum acacia, guar gum, xanthan gum, kaolin, bentonite, hectorite, tragacanth, sodium alginate, pectin, and the like.

Suitable anionic surfactants may be one or more of sodium dodecyl sulfate (SDS), sodium lauryl sulfate (SLS), sodium laurate, dialkyl sodium sulfosuccinates, sodium stearate, potassium stearate, sodium oleate, and the like.

Suitable cationic surfactants may be one or more of benzalkonium chloride, bis-2-hydroxyethyl oleyl amine, benzethonium chloride, cetrimide, and the like.

Suitable non-ionic surfactants may be one or more of poloxamers, polyoxyethylene sorbitan fatty acid esters, fatty alcohols such as lauryl, cetyl and stearyl alcohols; glyceryl esters such as the naturally occurring mono-, di-, and triglycerides; fatty acid esters of fatty alcohols and other alcohols such as propylene glycol, polyethylene glycol, sorbitan, sucrose, cholesterol, and the like.

The term unmicronized fenofibrate as used herein refers to fenofibrate which is used as such and not subjected to size reduction by any means.

The pharmaceutical composition of the invention can be present in the form of a tablet, capsule, powder, disc, caplet, granules, pellets and other dosage forms suitable for oral administration. The tablets may further be coated with film forming polymers.

Examples of some film forming polymers that can be used for the coating include but are not limited to those known in the art, such as cellulose derivatives (hydroxypropyl methylcellulose, hydroxyethylcellulose, hydroxypropyl cellulose and their derivatives), acrylic and methacrylic copolymers of different molecular weights, and mixtures thereof.

The coating layers over the tablet may be applied as solution/dispersion of coating ingredients using conventional techniques known in the art selected from spray coating in a conventional coating pan or fluidized bed processor, dip coating, and the like.

The pharmaceutical compositions may include one or more pharmaceutically acceptable excipients from fillers, binders, lubricants, sweeteners, coloring and flavoring agents, glidants, disintegrants, and the like.

Suitable fillers may be one or more of microcrystalline cellulose, mannitol, calcium phosphate, calcium sulfate, kaolin, dry starch, powdered sugar, and the like.

Suitable binders may be one or more of povidone, starch, stearic acid, gums, hydroxypropylmethyl cellulose, and the like.

Suitable lubricants may be one or more of magnesium stearate, zinc stearate, calcium stearate, stearic acid, sodium stearyl fumarate, hydrogenated vegetable oil, glyceryl behenate, and the like.

Suitable glidants may be one or more of colloidal silicon dioxide, talc or cornstarch and the like.

Suitable disintegrants may be one or more of starch, croscarmellose sodium, crosspovidone, sodium starch glycolate, and the like.

The pharmaceutical composition of the invention can be prepared by mixing fenofibrate with one or more wetting agents, compacting the pre-mix through a compactor and sizing the flakes into granules. The granules thus obtained may be granulated with a binder, dried, mixed with other pharmaceutically acceptable excipients, or granules may be directly mixed with other pharmaceutically acceptable excipients, lubricated and compressed.

The pharmaceutical composition comprising unmicronized fenofibrate or a salt thereof in admixture with one or more wetting agents and one or more pharmaceutically acceptable excipients, wherein the mixture is not comicronized before processing; and wherein the formulation exhibits a dissolution profile such that more than 75% of fenofibrate is released within first 30 minutes, wherein the release rate is measured in Apparatus 2 (USP, Dissolution, paddle, 50 rpm) using 1000 ml of 0.05M SLS in water at 37° C. f 0.5° C.

The invention is further illustrated by the following examples which are provided merely to be exemplary of the invention and do not limit the scope of the invention. Certain modifications and equivalents will be apparent to those skilled in the art and are intended to be included within the scope of the invention.

EXAMPLE 1

The composition of batches is provided in Table 1. Following formulations are representatives of the preferred compositions of the invention. The preparation of example 1 is detailed below.

TABLE 1

Composition of Fenofibrate Tablets (48 mg, 145 mg)

| Sr. No. | Ingredients | Qty/tablet (% w/w) |
|---|---|---|
| | Part-I | |
| 1 | Fenofibrate (unmicronized) | 20-70 |
| 2 | Poloxamer | 5-50 |
| | Part-II | |
| 4 | Lactose | 20-70 |
| 5 | Silicified microcrystalline cellulose | 5-70 |
| 6 | Crospovidone | 1-6 |
| 7 | Povidone | 0.1-10 |
| 8 | Purified water | q.s. |
| 9 | Magnesium stearate | 0.1-3 |
| 10 | Opadry | 0.5-5 |

Procedure: Unmicronized fenofibrate and poloxamer were co-sifted and mixed in a double cone blender. The above pre-mix was compacted through a roll compactor and sizing was carried out to break flakes in to granules using a multi mill or oscillating granulator. The granules thus obtained were blended with pre-sifted lactose, silicified microcrystalline cellulose, crospovidone in a rapid mixer granulator and granulated with a binder solution in a rapid mixer granulator. The granules were dried, milled and blended with pre-sifted crospovidone. The granules were then lubricated with magnesium stearate and the final blend was compressed in to tablets using suitable tooling and coated with aqueous dispersion of Opadry.

EXAMPLE-2

The composition of the batches is provided in Table 2. Following formulations are representatives of the preferred compositions of the invention. The preparation of example 2 is detailed below.

TABLE 2

Composition of Fenofibrate Tablets (48 mg, 145 mg)

| Sr. No. | Ingredients | Qty/tablet (% w/w) |
|---|---|---|
|  | Part-I |  |
| 1 | Fenofibrate (unmicronized) | 20-70 |
| 2 | Poloxamer | 5-50 |
|  | Part-II |  |
| 4 | Lactose | 20-70 |
| 5 | Silicified microcrystalline cellulose | 5-70 |
| 6 | Crospovidone | 1-6 |
| 7 | Magnesium stearate | 0.1-3 |
| 8 | Opadry | 0.5-5 |

Procedure: Unmicronized fenofibrate and poloxamer were co-sifted and mixed in a double cone blender. The above pre-mix was compacted through a roll compactor and sizing was carried out to break flakes in to granules using a multi mill or oscillating granulator. The granules thus obtained were blended with pre-sifted lactose, silicified microcrystalline cellulose, crospovidone in a double cone blender and lubricated with magnesium stearate and the final blend was compressed in to tablets using suitable tooling and coated with aqueous dispersion of Opadry.

TABLE 3

Dissolution data of Fenofibrate tablets (145 mg)
Table 3 provides the dissolution data for fenofibrate tablets (145 mg) prepared as per the Formula given in Table 1 and 2. For determination of drug release rate, USP Type 2 Apparatus (rpm 50) was used wherein 1000 ml of 0.05M SLS in water at 37° C. ± 0.5° C. was used as medium.

| Time (min) | % drug released (Example-I) | % drug released (Example-II) |
|---|---|---|
| 10 | 25 | 31 |
| 20 | 60 | 66 |
| 30 | 80 | 83 |
| 45 | 92 | 96 |

While the invention has been described in terms of its specific embodiments, certain modifications and equivalents will be apparent to those skilled in the art and are intended to be included within the scope of the invention.

We claim:

1. A pharmaceutical composition comprising unmicronized fenofibrate at 20-70 (% w/w), poloxamer at 5-50 (% w/w), lactose at 20-70 (% w/w), silicified microcrystalline cellulose at 5-70 (% w/w), crospovidone at 1-6 (% w/w), povidone at 0.1-10 (% w/w), magnesium stearate, at 0.1-3 (% w/w), and opadry at 0.5-5 (% w/w).

2. A process for the preparation of a pharmaceutical composition according to claim 1, the process comprising:

a) mixing unmicronized fenofibrate with one or more wetting agents and optionally with one or more pharmaceutically acceptable excipients;

b) converting the pre-mix of step a) in to granules; and c) converting the granules of step b) in to a suitable dosage form.

* * * * *